United States Patent
Seemayer et al.

(10) Patent No.: US 6,600,062 B2
(45) Date of Patent: Jul. 29, 2003

(54) PREPARATION OF CHIRAL 6,7-DIHYDROXY GERANYLOXY COMPOUNDS

(75) Inventors: Robert Seemayer, Belmont, CA (US); Yian Shi, Fort Collins, CO (US)

(73) Assignees: DSM Catalytica Pharmaceuticals, Inc., Mountain View, CA (US); Colorado State University Research Foundation, Fort Collins, CO (US)

(*) Notice: Subject to any disclaimer, the term of this patent is extended or adjusted under 35 U.S.C. 154(b) by 19 days.

(21) Appl. No.: 10/027,815

(22) Filed: Dec. 20, 2001

(65) Prior Publication Data

US 2002/0095061 A1 Jul. 18, 2002

Related U.S. Application Data

(63) Continuation-in-part of application No. 09/982,827, filed on Oct. 22, 2001, which is a continuation-in-part of application No. 09/983,006, filed on Oct. 18, 2001, which is a continuation-in-part of application No. 09/663,390, filed on Aug. 10, 2000, now Pat. No. 6,369,245, which is a continuation-in-part of application No. 09/284,054, filed as application No. PCT/US97/18310 on Oct. 8, 1997, now Pat. No. 6,348,608.

(60) Provisional application No. 60/241,850, filed on Oct. 20, 2000, provisional application No. 60/148,904, filed on Aug. 13, 1999, and provisional application No. 60/028,009, filed on Oct. 8, 1996.

(51) Int. Cl.$^7$ .................. C07C 271/26; C07C 271/08

(52) U.S. Cl. .................. 560/33; 560/24; 560/164; 568/857; 568/875

(58) Field of Search .................. 560/33, 24, 164; 568/875, 857

(56) References Cited

PUBLICATIONS

Zhi–Xian Wang et al., *J. Am. Chem. Soc.*, 1997, 119, 11224–11235.
Lianhe Shu et al., *Tetrahedron Letters*, 1999, 40, 8721–8724.
H. Hirohara et al., *Biocatalysts in Organic Synthesis*, Proceedings of an International Symposium held at Noordwijkerhout, 1985, pp. 119–134.
Zhi–Xian Wang et al., *J. Org. Chem.*, 1998, 63, 3099–3104.
X. M. Zhang, et al., *J. Org. Chem.*, 1991, 56, 3814–3817.
J.D. Fourneron et al., *J. Org. Chem.*, 1989, 54, 4686–4689.
von Matthias Kamber et al., *Helvetica Chimica Acta*, 1984, 67, 968–985.
von Walter Eschenmoser et al., *Helvetica Chimica Acta*, 1983, 66, 82–91.
Dharmpal S. Dodd et al., *J. Org. Chem.*, 1992, 57, 7227–7234.
K. Barry Sharpless et al., *J. Org. Chem.*, 1992, 57, 2768–2771.
Mitsuaki Kodama et al., *Tetrahedron Letters*, 1990, 31, 4025–4026.
Deukjoon Kim et al., *Tetrahedron Letters*, 1990, 31, 4027–4028.
E. J. Corey et al., *Tetrahedron Letters*, 1993, 34, 5995–5998.

*Primary Examiner*—Ba K Trinh
(74) *Attorney, Agent, or Firm*—Townsend and Townsend and Crew LLP

(57) ABSTRACT

The present invention provides a method for enantioselectively producing a nonracemic 6,7-dihydroxy geranyloxy compound from a geranyloxy compound. In particular, methods of the present invention involve enantioselectively epoxidizing the geranyloxy compound and hydrolyzing the epoxide moiety under conditions sufficient to produce the nonracemic 6,7-dihydroxy geranyloxy compound.

26 Claims, No Drawings

PREPARATION OF CHIRAL 6,7-DIHYDROXY GERANYLOXY COMPOUNDS

This is a continuation-in-part of U.S. patent application Ser. No. 09/284,054, filed Apr. 6, 1999, now U.S. Pat. No. 6,348,608 which is a national phase application of PCT Patent Application No. PCT/US97/18310, filed Oct. 8, 1997, which claims the priority benefit of U.S. Provisional Patent Application No. 60/028,009, filed Oct. 8, 1996. This application is also a continuation-in-part of U.S. patent application Ser. No. 09/663,390, filed Aug. 10, 2000, now U.S. Pat. No. 6,369,245 which claims the priority benefit of U.S. Provisional Patent Application No. 60/148,904, filed Aug. 13, 1999. All of the above mentioned applications are incorporated herein by reference in their entirety. This application is also a continuation-in-part of U.S. patent application Ser. No. 09/982,827, filed Oct. 22, 2001, now pending which claims the priority benefit of U.S. Provisional Patent Application No. 60/241,850, filed Oct. 20, 2000. This application is also a Continuation-in-part of U.S. patent application Ser. No. 09/983,006, filed Oct. 18, 2001 now pending.

FIELD OF THE INVENTION

This invention relates to a method of stereoselectively producing 6,7-dihydroxy geranyloxy compounds.

BACKGROUND OF THE INVENTION

Dihydroxy geranyloxy moieties are present in a variety of pharmaceutically active compounds, including, but not limited to, 6,7-dihydroxybergamottin, and compounds such as those disclosed in U.S. Pat. Nos. 5,990,154; 6,054,477; 6,063,809; 6,124,477; 6,162,479; and 6,248,776. In particular, 6,7-dihydroxy geranyloxy moiety is present in many of these pharmaceutically active compounds.

6,7-Dihydroxy geranyloxy moiety comprises a chiral center, and it is well known that the stereochemistry of a molecule is important in many of the properties of the molecule. For example, physiological properties of pharmaceutically active compounds having one or more chiral centers, i.e., stereochemical centers, can depend on the stereochemistry of the compound's chiral center.

Therefore, there is a need for a method of stereoselectively producing 6,7-dihydroxy geranyloxy moiety.

SUMMARY OF THE INVENTION

One aspect of the present invention provides a method for enantioselectively producing a nonracemic dihydroxy geranyloxy compound from a geranyloxy compound. In particular, methods of the present invention utilize an asymmetric epoxidation reaction to selectively epoxidize the olefin moiety in the 6,7-position of the geranyloxy moiety. The resulting nonracemic epoxide is then hydrolyzed to produce a nonracemic 6,7-dihydroxy geranyloxy compound.

The enantiomeric excess of the nonracemic 6,7-dihydroxy geranyloxy compound can be further increased (i.e., enriched) by increasing the enantiomeric excess of the nonracemic 6,7-epoxy geranyloxy compound prior to hydrolyzing the epoxide moiety. When the 6,7-epoxy geranyloxy compound is a solid, enantiomeric excess enrichment can be achieved by crystallization, and optionally by recrystallization. The enantiomeric excess of the nonracemic 6,7-dihydroxy geranyloxy compound can be further increased after it is produced by the epoxide hydrolysis reaction step. When the 6,7-dihydroxy geranyloxy compound is a solid, enantiomeric excess enrichment can be achieved by crystallization, and optionally by recrystallization.

DEFINITIONS

"Geranyloxy compound" refers to any compound which comprises a geranyloxy moiety of the formula:

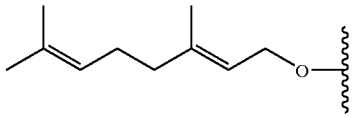

Geranyloxy compounds include, but are not limited to, geraniol, geranyl ethers, geranyl esters of organic and inorganic acids, geranyl carbonates, and geranyl carbamates, as defined herein.

"Epoxy geranyloxy compound" refers to any compound which comprises a geranyloxy moiety, as defined herein, in which one or both, preferably one, of the olefins in the geranyloxy moiety have been epoxidized.

"6,7-dihydroxy geranyloxy compound" refers to a geranyloxy compound as defined herein in which the 6,7-position of the geranyloxy moiety comprises hydroxyl groups, i.e., compound comprising a moiety of the formula:

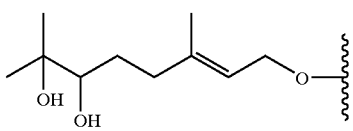

"Hydrolyzing" refers to opening the epoxide ring moiety by the addition of a molecule of water to provide a vic-diol. For example, hydrolyzing a 6,7-epoxide geranyloxy compound to produce a 6,7-dihydroxy geranyloxy compound.

"Peracid" has the usual meaning in the art and refers to any oxyacid compound wherein the —OH group is replaced with the —OOH group. Peracids include percarboxylic acids (e.g., meta-chloroperbenzoic acid), persulfuric acid ($H_2SO_5$), and imidoperacids (e.g., $CH_3$—C(=NH)—OOH). As used herein, the term "peracid" includes salts of peracids (e.g., potassium bipersulfate, $KHSO_5$).

"Peroxyimidate" (also known as imidoperacid) refers to an oxidizing agent which is produced from a mixture of an oxidizing agent, preferably hydrogen peroxide, and a nitrile compound. Without being bound by any theory, it is believed that the mixture of hydrogen peroxide and a nitrile compound (e.g., R—CN) result in a peroxyimidate of the formula R—C(=NH)—OOH.

As used herein, the term "treating", "contacting" or "reacting" refers to adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

"Side-reaction" is a reaction that does not ultimately lead to a production of a desired product. For example, a desired product of the reaction comprising an oxidizing agent, a ketone and an olefin is an epoxide.

"Chiral center", i.e., stereochemical center or stereogenic center, is, of course, an atom to which four different groups are attached. However, the ultimate criterion of a chiral center is nonsuperimposability on the mirror image.

"Facially selective," "stereoselective," "enantioselective" or "asymmetric" synthetic reactions are those in which one of a set of stereoisomers is formed exclusively or predominantly.

"Crystallization" refers to a purification process of isolating a solid from the reaction mixture or an extraction solution.

"Recrystallization" refers to a further purification process of an isolated solid, whereby the solid is dissolved in a crystallizing solution and is recrystallized to provide a solid of higher purity.

DETAILED DESCRIPTION

One aspect of the present invention provides a method for enantioselectively producing a dihydroxy geranyloxy compound from a geranyloxy compound utilizing an asymmetric epoxidation reaction and hydrolyzing the resulting nonracemic epoxy geranyloxy compound to produce a nonracemic dihydroxy geranyloxy compound. In particular, the present invention is directed to enantioselectively producing a nonracemic 6,7-dihydroxy geranyloxy compound.

Methods of the present invention comprise:

(a) contacting a reaction mixture comprising the geranyloxy compound with an oxidizing agent in the presence of a nonracemic chiral ketone under conditions sufficient to enantioselectively produce a nonracemic 6,7-epoxy geranyloxy compound; and (b) hydrolyzing the epoxide moiety of the nonracemic 6,7-epoxy geranyloxy compound under conditions sufficient to produce the nonracemic 6,7-dihydroxy geranyloxy compound.

Epoxidation of an olefin is a useful synthetic reaction in the field of organic chemistry. Such reaction has been used frequently in the preparation of an intermediate and/or the final product of many pharmaceutically active compounds. Many epoxidation reactions have been developed over the years including asymmetric epoxidations. Some of these epoxidation reactions require the use of transition metals or other heavy metals which are potentially harmful even in trace amounts. Still others methods require expensive reagents which significantly increase the overall cost of epoxidation reaction. Methods of the present invention avoid these problems by using an asymmetric epoxidation reaction that is based on a combination of an oxidizing agent and a chiral ketone compound.

Without being bound by any theory, it is believed that a reaction between the oxidizing agent and a ketone generates a dioxirane, which is believed to be the reactive species that epoxidizes the geranyloxy compound. By using a nonracemic chiral ketone, one can affect an asymmetric epoxidation of the geranyloxy compound, thereby producing a nonracemic epoxy geranyloxy compound.

It is also believed that the reaction between the geranyloxy compound and the dioxirane provides a nonracemic epoxy geranyloxy compound and regenerates the nonracemic chiral ketone; therefore, the nonracemic chiral ketone can be used in a catalytic amount. Thus, in one particular embodiment of the present invention, less than one equivalent of the nonracemic chiral ketone relative to the amount of the geranyloxy compound is used in the present invention. Preferably, methods of the present invention use about 1 equivalent or less of the nonracemic chiral ketone, more preferably about 0.3 equivalent or less, and most preferably about 0.1 equivalent or less.

Use of a nonracemic chiral ketone provides nonracemic 6,7-epoxy geranyloxy compound. Preferably, the chiral ketones which are used in methods of the present invention are cyclic chiral ketones. The cyclic chiral ketones can optionally comprise one or more heteroatoms, such as oxygen, nitrogen and sulfur, within the cyclic structure. Useful chiral ketones include a variety of chiral ketones disclosed by Denmark and Wu in *Synlett*. 1999, 847, and by Shi in PCT Publication No. WO 98/15544, which are incorporated herein by reference in their entirety. In one particular embodiment, the chiral ketone is 1,2:4,5-di-O-isopropylidene-β-D-erythro-2,3-hexodiulo-2,6-pyranose, i.e., a compound of the formula:

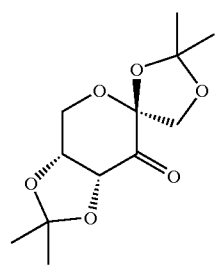

I or a stereo isomer thereof.

When chiral ketone of Formula I is used, the resulting 6,7-epoxy geranyloxy compound is enantiomerically enriched with the (R)-6,7-epoxy geranyloxy compound. Preferably, use of chiral ketone of Formula I provides (R)-6,7-epoxide geranyloxy compound with the enantiomeric excess of at least about 50% ee, more preferably with the enantiomeric excess of at least about 60% ee, and most preferably with the enantiomeric excess of at least about 70% ee.

As expected, in general a higher enantiomeric purity of the chiral ketone leads to a higher enantioselectivity of the epoxidation reaction, i.e., higher % ee of the 6,7-epoxy geranyloxy compound. Thus, typically, the enantiomeric excess of the chiral ketone that is used in methods of the present invention is at least about 80% ee. Preferably, the enantiomeric excess of the chiral ketone that is used in methods of the present invention is at least about 90% ee, and more preferably at least about 95% ee.

The concentration of each reagent can affect the reaction rate of the epoxidation reaction. Generally, a higher reagent concentration results in a higher reaction rate. However, in general, as the reagent concentration increases potential for a side-reaction also increases. Without being bound by a theory, it is believed that one of the undesired side-reaction is the Baeyer-Villiger reaction. Thus, a typical concentration of the geranyloxy compound in the reaction mixture is from about 0.01 mole/liter (M) to about 5 M. Preferably, the concentration of the geranyloxy compound in the epoxidation reaction is from about 0.1 M to about 1 M, and more preferably from about 0.1 M to about 0.5 M.

The pH of the reaction mixture can also influence the epoxidation reaction rate and/or the product yield. The pH of the reaction solution can be conveniently adjusted by adding a sufficient amount of base to maintain the pH at the desired level. The base can be added separately, all at once or in portions during the reaction. Preferably, the base is selected from the group consisting of hydroxides, carbonates, bicarbonates, borates and phosphates. More preferably, the base is selected from the group consisting of potassium carbonate, potassium bicarbonate, lithium carbonate, lithium bicarbonate, sodium carbonate, cesium carbonate, rubidium carbonate, sodium bicarbonate, calcium carbonate, sodium borate, sodium phosphate, potassium phosphate, lithium hydroxide, sodium hydroxide, potassium hydroxide, magnesium hydroxide and calcium hydroxide. And most preferably, the base is selected from the group consisting of potassium carbonate, potassium bicarbonate, sodium bicarbonate, sodium carbonate, sodium hydroxide, sodium borate, sodium phosphate, potassium phosphate and potassium hydroxide. Alternatively, the desired pH of the reaction can be maintained by using a buffer solution.

In general, a relatively high pH provides a higher conversion rate of the geranyloxy compound to the 6,7-epoxy geranyloxy compound and/or higher catalytic efficiency (i.e., higher turn-over rate of the ketone). Typically, the pH of the reaction mixture is maintained at about pH 5 or higher, preferably at about pH 8 or higher, and more preferably at about pH 10 or higher. In particular, the pH of the reaction mixture is generally maintained at from about pH 5 to about pH 14, preferably at from about pH 10 to about pH 14, and more preferably at from about pH 10 to about pH 12.

The reaction time can affect the yield of and/or the enantiomeric excess of the 6,7-epoxy geranyloxy compound. Thus, in some cases while a longer reaction period provides a higher yield of the 6,7-epoxy geranyloxy compound, its enantiomeric excess begins to decrease after a period of time. Therefore, obtaining a maximum yield of the 6,7-epoxy geranyloxy compound while maintaining a sufficient level of its enantiomeric excess sometimes requires a compromise between the two diametrically opposed results.

The reaction temperature can affect the yield and the rate of the epoxidation reaction. Moreover, enantiomeric excess of the 6,7-epoxy geranyloxy compound can also be affected by the reaction temperature. Generally, a lower reaction temperature requires a longer reaction time but results in a higher enantioselectivity. In the present invention, the reaction temperature can range from about −10° C. to about 50° C. Typically, the epoxidation reaction temperature is from about 0° C. to 30° C. However, it should be appreciated that the present invention is not limited to these reaction temperature ranges.

Typically, the oxidizing agent is an oxygen transferring agent. Preferably, the oxidizing agent is a peroxy compound. More preferably, the oxidizing agent is selected from the group consisting of hydrogen peroxide, a peracid (e.g., peroxysulfuric acid), a salt of a peracid (e.g., a peroxysulfate salt), a peroxyimidate and a mixture thereof.

In one particular embodiment, the oxidizing agent compound is selected from peroxysulfuric acid, a peroxysulfate salt, and a mixture thereof.

In another embodiment, the oxidizing agent is a reaction product of the oxidizing agent, preferably hydrogen peroxide (typically 30% solution in water), and a nitrile compound. Without being bound by any theory, it is believed that using hydrogen peroxide in combination with a nitrile compound (e.g., R—CN) generates a peroxyimidate of the formula R—C(=NH)—OOH. It is believed that this peroxyimidate reacts with the nonracemic chiral ketone to generate the corresponding dioxirane which then epoxidizes the geranyloxy compound to produce the 6,7-epoxy geranyloxy compound.

The amount of hydrogen peroxide used in the present invention depends on a variety of factors including the reactivity of the nonracemic chiral ketone, the geranyloxy compound, and the nitrile compound. Typically, however, the amount of hydrogen peroxide used is at least about 1 equiv. relative to the amount of the geranyloxy compound. Typically, the amount of hydrogen peroxide used relative to the amount of the geranyloxy compound is from about 1 equiv. to about 10 equiv. Preferably from about 1 equiv. to about 5 equiv., and more preferably from about 2 equiv. to about 4 equiv.

The nitrile compound can be any compound containing a nitrile functional group (i.e., —CN functional group). Preferably, the nitrile compound does not contain other functional group which can react with other components of the reaction mixture. More preferably, the nitrile compound is of the formula R—CN, where R is $C_1$–$C_{10}$ alkyl, $C_3$–$C_{10}$ cycloalkyl, $C_6$–$C_{20}$ aryl or $C_7$–$C_{21}$ aralkyl. Preferably R is $C_1$–$C_6$ alkyl or $C_6$–$C_{15}$ aryl, and more preferably R is methyl, ethyl or phenyl (i.e., R—CN is acetonitrile, propionitrile, and benzonitrile respectively). Most preferred nitrile is acetonitrile.

The nitrile compound can be used as a solvent or it can be used as a reagent. Typically, a total of from about 1 equiv. to about 100 equiv. of the nitrile compound, relative to the total amount of the geranyloxy compound, is added to the reaction mixture. When the nitrile compound is used as a reagent, the total amount of nitrile compound added to the reaction mixture is typically about 1 equiv. to about 10 equiv. relative to the geranyloxy compound. Preferably from about 2 equiv. to about 4 equiv. However, the amount of the nitrile compound used in methods of the present invention is not limited to these ranges. Moreover, other oxidizing agents that are capable of producing a peroxyimidate from the corresponding nitrile compound can also be used instead of hydrogen peroxide. Typically, however, for economical reasons, both in terms of the cost and purification process, hydrogen peroxide is the preferred oxidizing agent.

When hydrogen peroxide is used as an oxidizing agent, water is present in the reaction mixture. Moreover, using other oxidizing agents, such as potassium monopersulfate, often requires dissolving it in water. Therefore, epoxidation reactions of the present invention are often conducted in a co-solvent system between an organic solvent and water. Generally, any organic solvent can be used. Exemplary organic solvents which are useful in the present invention include, but are not limited to, nitrites such as acetonitrile, propionitrile and benzonitrile, dimethoxymethane (DMM), dimethoxyethane (DME), ethers such as tetrahydrofuran (THF) and ether, dichloromethane, chloroform, ethyl acetate, hexane, benzene, toluene, xylenes, dioxane, dimethyl formamide (DMF), pentane, alcohols including, but not limited to, methanol, ethanol, butanol and i-propyl alcohol, and mixtures thereof. A particularly, preferred organic solvent when hydrogen peroxide is used as an oxidizing agent is a nitrile compound. Thus, the nitrile compound is used both as the co-solvent and as a reagent to generate the peroxyimidate in situ which then oxidizes the ketone to a corresponding dioxirane.

Epoxidation of the geranyloxy compounds can be performed in a variety of different sequences. The addition sequence of the geranyloxy compound, nonracemic chiral ketone, oxidizing agent (e.g., a mixture of hydrogen peroxide and the nitrile compound) and base (if any) can be interchanged depending on the nature of each reagent. When using a relatively unstable oxidizing agent, such as hydrogen peroxide or other labile oxidizing agent, it is preferred that the oxidizing agent be added slowly to the reaction mixture comprising the geranyloxy compound and the nonracemic chiral ketone. In such cases, the oxidizing agent is typically added over a period of from about 1 to about 8 hours. Preferably, the oxidizing agent is added over a period of from about 2 to about 4 hours.

In one particular embodiment of the present invention, the geranyloxy compound is a geranyl carbamate, preferably a geranyl N-aryl carbamate, and more preferably a geranyl N-phenyl carbamate. 6,7-Dihydroxy geranyl N-phenyl carbamate is a crystalline solid. Thus, the enantiomeric excess of the nonracemic 6,7-dihydroxy geranyl N-phenyl carbamate produced in the hydrolysis reaction step can be further increased by crystallizing the nonracemic 6,7-dihydroxy geranyl N-phenyl carbamate, and optionally further increased by recrystallizing it.

6,7-Epoxy geranyloxy compounds are useful intermediates in a variety of applications, including in the preparation of pharmaceutically active compounds. For example, a 6,7-epoxy geranyloxy compound can be ring opened to afford a 6,7-dihydroxy geranyloxy compound. There are many pharmaceutically active compounds which contain a 6,7-dihydroxy geranyloxy moiety, including 6,7-dihydroxybergamottin, and compounds such as those disclosed in U.S. Pat. Nos. 5,990,154; 6,054,477; 6,063,809; 6,124,477; 6,162,479; and 6,248,776.

Thus, in another embodiment of the present invention, the geranyloxy compound is bergamottin.

The geranyl moiety of the geranyloxy compound comprises two olefinic moieties at the 2,3- and 6,7-positions. It has been found by the present inventors that by selecting appropriate reaction conditions, methods of the present invention can provide regioselective epoxidation of the geranyloxy compound. Hence, in one particular embodiment, the 6,7-olefinic moiety of the geranyl moiety is epoxidized selectively to produce a 6,7-epoxy geranyloxy compound. Typically, methods of the present invention provide at least about 80% regioselective epoxidation of the 6,7-olefinic moiety of the geranyl moiety. Preferably, methods of the present invention provide regioselective epoxidation of at least about 90%, and more preferably at least about 95%. The % regioselectivity is calculated using the following formula:

$$(A-B)/(A+B)*100\%$$

where A=the amount of 6,7-epoxy geranyloxy compound and B=the amount of 2,3-epoxy geranyloxy compound.

Moreover, methods of the present invention typically provide the 6,7-epoxy geranyloxy compound with enantiomeric excess of at least about 50% ee. Preferably, methods of the present invention provide the 6,7-epoxy geranyloxy compound with enantioselectivity of at least about 60% ee, and more preferably at least about 70% ee.

It should be appreciated that when the geranyloxy compound comprises one or more stereochemical center, the resulting nonracemic 6,7-epoxy geranyloxy compound and the nonracemic 6,7-dihydroxy geranyloxy compound are diastereomers. However, for the sake of brevity and clarity, the terms "enantiomer", "enantiomeric excess" and "enantioselectivity" refer to the relative stereochemical center only on the geranyl moiety.

Methods of the present invention also include hydrolyzing the 6,7-epoxy geranyloxy compound to produce the 6,7-dihydroxy geranyloxy compound, i.e., epoxide ring opening reaction which adds net one molecule of water to a molecule of the epoxy geranyloxy compound. Hydrolysis of the epoxide moiety can be achieved under a wide variety of conditions, such as under acidic or basic conditions. Without being bound by any theory, it is believed that the stereochemistry of the epoxide opening reaction depends on whether the reaction generates an intermediate or a transition state that resembles a carbocation. Typically, reaction conditions favoring generation of a late transition state or a carbocation intermediate result in formation of a more stable carbocation having the positive charge on the 7-position of the geranyl moiety and addition of the nucleophile water to that position, because the 7-position affords more stable late transition state and a carbocation intermediate relative to the 6-position. Hydrolysis of the epoxide ring can be achieved under a wide variety of solvents, such as aqueous solvent, organic solvents, and mixtures thereof. Exemplary solvents include, but are not limited to, water, alcohols, dimethylsulfoxide (DMSO), dimethoxyethane (DME), tetrahydrofuran (THF), ether and combinations thereof, as well as other solvents known to one skilled in the art.

In general, the epoxide ring opening reaction under basic conditions results in inversion of the stereochemistry, because the 6-position is sterically less hindered than the 7-position of the geranyl moiety. In most nucleophilic substitution reactions, the nucleophile (e.g., $^-$OH group) approaches the 6,7-epoxy geranyl compound from a less sterically hindered 6-position resulting in inversion of the stereochemistry at the 6-position. Hydrolysis of the epoxide ring under basic conditions typically involves adding a hydroxide, such as sodium, potassium, lithium or calcium hydroxides.

Epoxide ring opening reactions of 6,7-epoxide geranyloxy compound under acidic conditions can result in stereochemical inversion, retention or combination of both. In one particular embodiment of the present invention, the 6,7-epoxide geranyloxy compound is hydrolyzed under conditions sufficient to provide 6,7-dihydroxy geranyloxy compound with substantially retention of stereochemistry. Preferably, at least about 50% of the 6,7-epoxide geranyloxy compound is hydrolyzed with retention of stereochemistry, more preferably at least about 80%, and most preferably substantially all (i.e., >99%) of the 6,7-epoxide geranyloxy compound is hydrolyzed with retention of stereochemistry.

A wide variety of acids can be used to hydrolyze the epoxide ring. As used herein, the term "acid" includes to both Bronstead-Lowry acids and Lewis acids. Any acid which has a relatively non-nucleophilic counter ion can be used in methods of the present invention. Exemplary suitable acids for hydrolyzing the epoxide ring include, but are not limited to, perchloric acid, sulfuric acid, phosphoric acid, acetic acid, trifluoroacetic acid, methanesulfonic acid, and the like. Preferably, perchloric acid is used to hydrolyze the epoxide ring.

As can be seen above, one can selectively open the epoxide ring either with retention or inversion of stereochemistry to produce the 6,7-dihydroxy geranlyoxy compound with a desired stereochemistry. For example, if (R)-6,7-dihydroxy geranlyoxy compound is desired, one can hydrolyze the (R)-6,7-epoxy geranyloxy compound with retention of stereochemistry or hydrolyze (S)-6,7-epoxy geranyloxy compound with inversion of stereochemistry. Conversely, if (S)-6,7-dihydroxy geranlyoxy compound is desired, one can hydrolyze the (S)-6,7-epoxy geranyloxy compound with retention of stereochemistry or hydrolyze (R)-6,7-epoxy geranyloxy compound with inversion of stereochemistry. In general, basic conditions afford stereochemical inversion, whereas acidic conditions afford stereochemical retention. In one particular embodiment of the present invention, the 6,7-epoxy geranyloxy compound is hydrolyzed with retention of stereochemistry.

The 6,7-epoxy geranyloxy compound can be hydrolyzed in the mixture in which it is produced by providing conditions sufficient for the hydrolysis to occur, for example, by acidification of the reaction mixture. This allows a "one-pot" synthesis of 6,7-dihydroxy geranyloxy compounds from the corresponding geranyloxy compound. Alternatively, the 6,7-epoxy geranyloxy compound can be separated from some or all of the components of the epoxidation reaction mixture prior to the hydrolysis step by any of the conventional separation methods known to one skilled in the art. Exemplary separation methods include, but are not limited to, extraction, distillation, crystallization, and chromatography.

While the present invention is illustrated in connection with directly converting the 6,7-epoxy geranyloxy compound to the corresponding 6,7-dihydroxy geranyloxy compound, it should be appreciated that the scope of the present invention is not limited to this direct transformation. For example, the 6,7-epoxy geranyloxy compound can be converted to a different 6,7-epoxy geranyloxy compound prior to the hydrolysis step by modifying or exchanging other functional group(s) that may be present. This is particularly useful in some instances where there is a functionalized moiety that is bound to oxygen at the 1-oxy position. Moreover, the scope of the invention also encompasses processes where the hydrolysis of the 6,7-epoxy geranyloxy compound is conducted under conditions that simultaneously or concomitantly result in a modification or exchange of the chemical group at the 1-oxy position. For example, hydrolysis of a hydrolytically labile group bound to oxygen at the 1-oxy position can result in production of 6,7-dihydroxygeraniol.

The enantiomeric excess of the 6,7-epoxy geranyloxy compound can be increased prior to hydrolyzing the epoxide moiety. Such enantiomeric enrichment can be achieved by any of the conventional methods known to one skilled in the art. Exemplary enantiomeric enrichment methods include, but are not limited to, chromatography using a chiral stationary phase; converting to a diastereomeric mixture and separating the diastereomers; enzymatic chiral resolution; kinetic resolution; and selective crystallization. Crystallization, and optionally recrystallization, is particularly useful when the 6,7-epoxy geranyloxy compound is a solid, as this process allows simple and efficient method of enantiomeric enrichment of a relatively large quantity of 6,7-epoxy geranyloxy compound.

The enantiomeric excess of the 6,7-dihydroxy geranyloxy compound can also be increased after it is produced in the epoxide hydrolysis reaction step. Such enantiomeric enrichment can be achieved by any of the conventional methods known to one skilled in the art, such as those disclosed herein. Crystallization, and optionally recrystallization, is particularly useful when the 6,7-dihydroxy geranyloxy compound is a solid, as this process allows simple and efficient method of enantiomeric enrichment of a relatively large quantity of 6,7-dihydroxy geranyloxy compound.

Additional objects, advantages, and novel features of this invention will become apparent to those skilled in the art upon examination of the following examples thereof, which are not intended to be limiting.

EXAMPLES

Exemplary methods for enantioselective epoxidation reactions of geraniol and geranyl tributylsilyl ether using potassium monopersulfate as the oxidizing agent and 1,2:4,5-di-O-isopropylidene-β-D-erythro-2,3-hexodiulo-2,6-pyranose as the nonracemic chiral ketone is disclosed by one of the inventors of the present invention in *J. Org. Chem.* 63 (1998), 3009–3104, which is incorporated herein by reference in its entirety.

EXAMPLE 1

This example illustrates synthesis of (R)-6,7-dihydroxygeranyl N-phenylcarbamate from geranyl N-phenylcarbamate.

To a solution of 13.67 g (50 mmol) of geranyl N-phenylcarbamate in 150 mL of acetonitrile was added 50 mL of 1.0 M potassium carbonate solution and 1.28 g (5 mmol) of 1,2:4,5-di-O-isopropylidene-β-D-erythro-2,3-hexodiulo-2,6-pyranose. The solution was stirred at 25° C. and 20.0 mL (195 mmol) of 30% hydrogen peroxide was added dropwise by a syringe pump at a constant rate over 2 hours. The solution was stirred for an additional 0.5 hour, for a total of 2.5 hours. A sample was then taken and analyzed by chiral hplc, collecting area % data by UV detection at 235 nm, showing the presence of the 6,7-epoxygeranyl N-phenylcarbamate with 76% enantiomeric excess of the (R)-configuration. The reaction solution was partitioned between 250 mL of ethyl acetate and 250 mL of brine. The separated ethyl acetate solution was dried with sodium sulfate, then evaporated to yield 15.55 g of a yellow oil comprising 6,7-epoxygeranyl N-phenylcarbamate.

The oil was dissolved in 200 mL of tetrahydrofuran and 50 mL of water and treated with 1 mL 70% perchloric acid. After one hour at room temperature, the solution was partitioned between 250 mL of ethyl acetate and 250 mL of saturated aqueous sodium bicarbonate. The separated ethyl acetate solution was dried with sodium sulfate, then evaporated to yield 16.75 g of a yellow solid comprising 6,7-dihydroxygeranyl N-phenylcarbamate. Chiral hplc analysis showed the material to be 72% pure with 71% enantiomeric excess of the (R)-configuration.

The yellow solid was dissolved and crystallized from toluene to obtain 8.92 g (58% yield) of 6,7-dihydroxygeranyl N-phenylcarbamate as colorless crystals. Chiral hplc analysis showed the material to be 97% pure with 88% enantiomeric excess of the (R)-configuration. The absolute configuration was confirmed to be R by optical rotation ($[a]^D_{20}$=+19.1°, 1.914 g per 100 ml methanol; lit. S-6,7-dihydroxygeranyl N-phenylcarbamate: $[a]^D_{20}$=−18.46°, 1.93 g per 100 ml methanol).

EXAMPLE 2

This example illustrates synthesis of (R)-6',7'-dihydroxybergamottin from bergamottin using hydrogen peroxide as the oxidizing agent.

To a solution of 3.40 g (10 mmol) of bergamottin in 25 mL of acetonitrile was added 10 mL of 1.45 M potassium carbonate solution and 0.80 g (3.1 mmol) of 1,2:4,5-di-O-isopropylidene-β-D-erythro-2,3-hexodiulo-2,6-pyranose. The solution was stirred at room temperature and 8.0 mL (78 mmol) of 30% hydrogen peroxide was added dropwise by a syringe pump at a constant rate over 4 hours. A sample was then taken and analyzed by chiral hplc, showing 92% conversion to 6',7'-epoxybergamottin with a 78% enantiomeric excess of the (R)-configuration. The reaction solution was partitioned between ethyl acetate and brine. The separated ethyl acetate solution was dried with sodium sulfate, then evaporated to yield crude 6',7'-epoxybergamottin.

The crude 6',7'-epoxybergamottin (2 g) was dissolved in 20 mL of tetrahydrofuran and 1 mL of 3% aqueous perchloric acid was added. After two hours at room temperature, thin layer chromatography showed complete conversion of the 6',7'-epoxybergamottin. The solution was partitioned between ethyl acetate and brine. The separated ethyl acetate solution was dried with sodium sulfate, then evaporated to yield crude product. The crude product was purified by flash chromatography. Chiral hplc analysis of the purified product showed the material to be 6',7'-dihydroxybergamottin with a 77% enantiomeric excess of the (R)-configuration.

EXAMPLE 3

This example illustrates synthesis of (R)-6',7'-dihydroxybergamottin from bergamottin using potassium monopersulfate as the oxidizing agent.

Bergamottin (337 mg, 1.0 mmol) was dissolved in 20 mL of acetonitrile and 10 mL of an aqueous solution of 0.05 M $Na_2B_2O_7$ and 0.4 mM $Na_2EDTA$. To this solution was added 15 mg (0,04 mmol) of tetrabutylammonium bisulfate, followed by 77.4 mg (0.30 mmol) of 1,2:4,5-di-O-isopropylidene-β-D-erythro-2,3-hexodiulo-2,6-pyranose, and the mixture was cooled to 0° C. Using a dual channel syringe pump, a solution of 800 mg (5.8 mmol) of potassium carbonate in 6.5 mL of water and a solution of 850 mg (1.38 mmol) Oxone® ($2KHSO_5 \cdot KHSO_4 \cdot K_2SO_4$) in 6.5 mL of 0.4 mM $Na_2EDTA$ aqueous solution were simultaneously added over 1.5 hours. The reaction mixture was diluted with 30 mL of water and 30 mL of heptane. The aqueous layer was separated and extracted with 2×20 mL of heptane. The organic layers were combined, dried with sodium sulfate and concentrated under vacuum to yield 360 mg of a brown oil. HPLC analysis showed a 57:27 mixture of 6',7'-epoxybergamottin and unreacted bergamottin. Chiral HPLC analysis showed the 6',7'-epoxybergamottin to have a 80% enantiomeric excess of the (R)-configuration.

The brown oil was taken up in 8 mL of tetrahydrofuran, 2 mL of water and 0.1 mL of 70% perchloric acid and the mixture was stirred at room temperature overnight. The reaction mixture was diluted with 20 mL of methylene chloride and 20 mL of saturated aqueous sodium bicarbonate solution. The organic layer was separated, dried with disodium sulfate and concentrated under high vacuum to yield 320 mg of a yellow oil comprising 6',7'-dihydroxybergamottin. Chiral HPLC analysis showed the 6',7'-dihydroxybergamottin to have a 86% enantiomeric excess of the (R)-configuration.

EXAMPLE 4

This example illustrates synthesis of (R)-6,7-dihydroxygeranyl 3,5-dinitrobenzoate.

To a solution of geranyl 3,5-dinitrobenzoate (3.48 g, 10 mmol) in 40 mL of acetonitrile was added 10 mL of 1.0 M potassium carbonate solution and 0.77 g (3.0 mmol) of 1,2:4,5-di-o-isopropylidene-β-D-erythro-2,3-hexodiulo-2,6-pyranose. The solution was stirred at 25° C. and 8.0 mL (78 mmol) of 30% hydrogen peroxide was added dropwise by a syringe pump at a constant rate over 4 hours. The solution was stirred for a total of 18 hours. The reaction mixture was diluted with 50 mL of ethyl acetate and 50 mL of aqueous brine solution. The aqueous layer was separated, and extracted with 50 mL of ethyl acetate. The organic layers were combined, dried with disodium sulfate and concentrated under vacuum to yield 3.54 g crude (>90%)6,7-epoxygeranyl 3,5-dinitrobenzoate as an orange solid. Chiral HPLC analysis showed the 6,7-epoxygeranyl 3,5-dinitrobenzoate to have a 74% enantiomeric excess of the (R)-configuration.

The crude 6,7-epoxygeranyl 3,5-dinitrobenzoate (364 mg) was dissolved in 10 mL of tetrahydrofuran and 2.5 mL of water. The mixture was cooled to 0° C. and 40 μL of 70% perchloric acid was added, and the solution was allowed to warm to room temperature and stirred overnight. The reaction mixture was diluted with 20 mL of methyl t-butyl ether and 20 mL of saturated aqueous sodium bicarbonate solution. The organic layer was separated, dried with disodium sulfate and concentrated to obtain crude (92% purity) 6,7-dihydroxygeranyl 3,5-dinitrobenzoate with a 72% enantiomer excess of the (R)-configuration. The crude material was purified by flash chromatography on silica with elution with first 1:1 heptane:methyl t-butyl ether, then methyl t-butyl ether. Fractions containing 6,7-dihydroxygeranyl 3,5-dinitrobenzoate were combined and concentrated to yield 340 mg (0.89 mmol) of 6,7-dihydroxygeranyl 3,5-dinitrobenzoate as a colorless solid (89% yield from the epoxide).

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method for enantioselectively producing a nonracemic 6,7-dihydroxy geranyloxy compound, said method comprising:
    (a) epoxidizing a geranyloxy compound by contacting a reaction mixture comprising the geranyloxy compound with an oxidizing agent in the presence of a nonracemic chiral ketone under conditions sufficient to enantioselectively produce a nonracemic 6,7-epoxy geranyloxy compound, and
    (b) hydrolyzing the epoxide moiety of the nonracemic 6,7-epoxy geranyloxy compound under conditions sufficient to produce the nonracemic 6,7-dihydroxy geranyloxy compound.

2. The method of claim 1, wherein the enantiomeric excess of the nonracemic 6,7-dihydroxy geranyloxy compound is at least about 50%.

3. The method of claim 1, wherein the geranyloxy compound is a geranyl carbamate.

4. The method of claim 3, wherein the geranyl carbamate is an N-aryl geranyl carbamate.

5. The method of claim 4, wherein the N-aryl geranyl carbamate is an N-phenyl geranyl carbamate.

6. The method of claim 5 further comprising:
    (c) increasing the enantiomeric excess of the nonracemic 6,7-dihyroxy geranyloxy compound.

7. The method of claim 6, wherein said step of increasing the enantiomeric excess of the nonracemic 6,7-dihyroxy geranyloxy compound comprises crystallizing the nonracemic 6,7-dihyroxy geranyloxy compound.

8. The method of claim 1, wherein said step of hydrolyzing the epoxide moiety of the nonracemic 6,7-epoxy geranyloxy compound comprises acidic conditions which produces the nonracemic 6,7-dihydroxy geranyloxy compound with retention of stereochemistry.

9. The method of claim 1, wherein the oxidizing agent is a peroxy compound.

10. The method of claim 9, wherein the peroxy compound is selected from a peracid, a salt of peracid, hydrogen peroxide, a peroxyimidate, and a mixture thereof.

11. The method of claim 10, wherein the peroxy compound is selected from peroxysulfuric acid, a peroxysulfate salt, and a mixture thereof.

12. The method of claim 10, wherein the peroxy compound is a peroxyimidate generated in situ from hydrogen peroxide and a nitrile compound.

13. The method of claim 12, wherein the nitrile compound is acetonitrile.

14. The method of claim 1, wherein the enantiomeric excess of the nonracemic chiral ketone is at least about 80%.

15. The method of claim 1, wherein the nonracemic chiral ketone is of the formula:

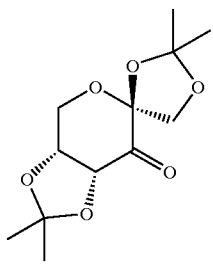

or a stereoisomer thereof.

16. The method of claim 15, wherein the nonracemic chiral ketone is of the formula:

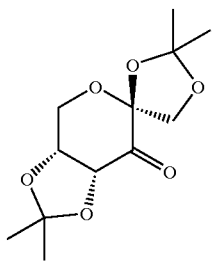

and the nonracemic 6,7-dihydroxy geranyloxy compound has a (R)-stereochemical configuration.

17. A method for enantioselectively producing a (R)-6,7-dihydroxy geranyloxy compound, said method comprising:
(a) epoxidizing a geranyloxy compound by contacting a reaction mixture comprising the geranyloxy compound with an oxidizing agent in the presence of a nonracemic chiral ketone under conditions sufficient to enantioselectively produce a nonracemic (R)-6,7-epoxy geranyloxy compound, and
(b) hydrolyzing the epoxide moiety of the nonracemic (R)-6,7-epoxy geranyloxy compound under conditions sufficient to produce the nonracemic (R)-6,7-dihydroxy geranyloxy compound.

18. The method of claim 17, wherein the geranyloxy compound is a geranyl carbamate.

19. The method of claim 18, wherein the geranyl carbamate is an N-aryl geranyl carbamate.

20. The method of claim 19, wherein the N-aryl geranyl carbamate is an N-phenyl geranyl carbamate.

21. The method of claim 17, wherein the oxidizing agent is derived from a mixture comprising a nitrile compound and hydrogen peroxide.

22. The method of claim 21, wherein the nitrile compound is acetonitrile.

23. The method of claim 17, wherein the enantiomeric excess of the nonracemic chiral ketone is at least about 80%.

24. The method of claim 17, wherein the nonracemic chiral ketone is of the formula:

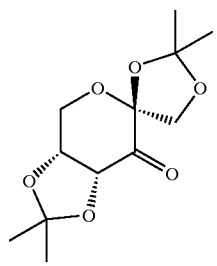

25. The method of claim 17, wherein the (R)-6,7-epoxy geranyloxy compound produced in said step (a) has an enantiomeric excess of at least about 70% ee.

26. The method of claim 17, wherein the geranyloxy compound is bergamottin.

* * * * *